(12) United States Patent
Papay et al.

(10) Patent No.: US 6,423,019 B1
(45) Date of Patent: Jul. 23, 2002

(54) CRANIAL REMODELING HEADPIECE

(75) Inventors: Francis A. Papay, Westlake; Michael M. Maierson, Seven Hills, both of OH (US)

(73) Assignee: Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 09/462,273

(22) PCT Filed: Feb. 20, 1998

(86) PCT No.: PCT/US98/03368

§ 371 (c)(1),
(2), (4) Date: Nov. 22, 1999

(87) PCT Pub. No.: WO98/36712

PCT Pub. Date: Aug. 27, 1998

Related U.S. Application Data

(60) Provisional application No. 60/038,455, filed on Feb. 20, 1997.

(51) Int. Cl.[7] ................................................. A61F 5/00
(52) U.S. Cl. ............................................................ 602/17
(58) Field of Search ................................. 128/857, 889; 2/410, 411, 412; 602/5, 12, 14, 17, 18; D29/102

(56) References Cited

U.S. PATENT DOCUMENTS

| | | | | |
|---|---|---|---|---|
| 2,151,458 A | * | 3/1939 | Allen | |
| 4,035,846 A | * | 7/1977 | Jencks | 2/413 |
| 4,776,324 A | * | 10/1988 | Clarren | 602/17 |
| 5,014,365 A | * | 5/1991 | Schulz | 2/412 |
| 5,094,229 A | * | 3/1992 | Pomatto et al. | 602/17 |
| 5,123,408 A | * | 6/1992 | Gaines | 602/17 |
| 5,218,975 A | * | 6/1993 | Prostkoff | 128/857 |
| 5,261,125 A | * | 11/1993 | Cartwright et al. | 2/421 |
| 5,308,312 A | * | 5/1994 | Pomatto et al. | 602/17 |
| 5,378,042 A | | 1/1995 | Daneshvar | |
| 5,549,678 A | * | 8/1996 | Prostkoff | 623/16 |
| 5,720,051 A | * | 2/1998 | Johnson | 2/413 |
| 5,951,503 A | * | 9/1999 | Pomatto | 602/17 |
| RE36,583 E | * | 2/2000 | Pomatto | 602/17 |

* cited by examiner

Primary Examiner—Kim M. Lewis
(74) Attorney, Agent, or Firm—Tarolli, Sundheim, Covell, Tummino & Szabo L.L.P.

(57) ABSTRACT

A cranial remodeling orthosis (10) for inducing directed growth and remodeling of an irregularly shaped skull (12). The orthosis (10) comprises a headpiece (14) having an outer wall (18) and an inner wall (16), the inner wall (16) being shaped to receive the skull (12) and having at least one recess (26) formed therein to provide a volume into which the skull (12) may be remodeled. The orthosis (10) further comprises a first expandable bladder (20) located on the inner wall (16) of the headpiece (14) whereby when the orthosis (10) is placed on the skull (12) and the bladder (20) is expanded, the recess (26) and the expanded bladder (20) cooperate to cause cranial remodeling.

31 Claims, 5 Drawing Sheets

CRANIAL REMODELING HEADPIECE

This application claims the benefit of provisional application No. 60/038,455 filed Feb. 20, 1997.

TECHNICAL FIELD

This invention relates to an improved orthotic headpiece, and more specifically to a cranial remodeling orthosis.

BACKGROUND OF THE INVENTION

Abnormal head shapes, known as positional plagiocephaly, may result from forces applied to an infant's head during the birthing process. Abnormal head shapes may also result from improper postnatal positioning of the infant's head. Infants having an abnormal skull shape or positional plagiocephaly may also have multistructural asymmetry in the cranium, cranial base, or the anterior craniofacial skeleton, including the orbits and external ear. A variety of factors, such as a premature birth, restrictive intrauterine environment, birth trauma, cervical anomalies, chronic sleeping positions and torticollis or chronic malpositioning of the neck due to muscle contracture have been found to increase the incident rate for these positional craniofacial deformations. The time required to produce postnatal deformation of the cranium depends upon skull compliance and pliability, and can range from several weeks to several months depending on the child's age.

Significant skull deformities that are not craniosynostotic in nature may be addressed through surgery of the cranial vault. Alternately, non-surgical intervention, in which forces are applied to the skull to allow directed growth and/or induce deformation, may be utilized. In the latter case, external cranial orthoses may be used to form the desired skull shape.

It is known to use an external cranial headpiece to apply forces to the skull to achieve skull remodeling. This is accomplished by fabricating a therapeutic headpiece based on a plaster of paris impression of the infant's head. The impression is then filled with a plaster slurry to create a positive mold of the head. An overlying headpiece is then made over the positive mold, and internal cavities are created to provide recesses into which the skull may grow/deform in a directed manner. In addition, dynamic orthotic cranioplasty has also been developed which utilizes a headpiece having external banding. The band encircles the cranium and may be tightened or loosened as desired to adjust the applied pressure. However, the headpiece of this device is not adjustable to accommodate growth of the child's head or the changing shape of the skull. As a result, a succession of new headpieces must be fabricated as the treatment progresses.

Another disadvantage in the prior art devices is that there is no manner in which to measure the force applied by the orthosis. Thus, the pressure may be set too high and cause pressure sores under the regions of high pressure. This problem is particularly troublesome due to the fact that cranial remodeling is performed primarily on infants who are unable to communicate effectively. Furthermore, the prior art headpieces may not allow for local adjustments of the pressure applied to the skull. Accordingly, the pressure applied by the headpiece should be set to a level below that which compromises perfusion to the scalp tissue, which may result in slower remodeling and prolonged treatment.

SUMMARY OF THE INVENTION

The device of the present application is an improved cranial remodeling orthosis. Specifically, the invention uses either expandable bladders such as hydraulic or pneumatic bladders inside a headpiece or helmet encircling the cranium to exert forces on the frontal, occipital, parietal, or other bony regions of the cranium. In a preferred embodiment, the bladders and band or headpiece are clear to enable visual inspection of the child's head. This allows the care giver to ensure proper fit of the headpiece and proper circulation to the scalp.

With the device of the present invention the bladders inside the headpiece can be inflated to the highest desirable level which still permits adequate blood perfusion. The present device allows visual inspection of the scalp to detect if the pressure is too high. Additionally, the bladders utilized in the invention may be expanded to a specific level so that the pressure is applied in a more controlled and precise manner than in the prior art devices discussed above. The use of pressure gauges or blood flow gauges allow for further monitoring of the infant's condition.

In the present device, air is expanded into preferably clear pneumatic bladders as the skull remodeling occurs. This allows the scalp to be monitored continuously throughout the therapy while corrective pressure is constantly or intermittently applied. The present invention also allows for an infant's care givers to monitor and control the pressure applied by the orthosis. With the past devices, the addition of pressure involved the decreasing of internal volume, addition of internal padding, tightening of screws, clamps or adding elastics to the external banding cranial orthosis, and usually required trained medical personnel.

The present invention is a cranial remodeling orthosis for inducing directed growth and remodeling of an irregularly shaped skull. The orthosis comprises a headpiece having an outer wall and an inner wall, the inner wall being shaped to receive the skull and having at least one recess formed therein to provide a volume into which the skull may be remodeled or growth directed. The orthosis further comprises a first expandable bladder located on the interior wall of the headpiece whereby when the orthosis is placed on the skull and the bladder is expanded, the recess and the expanded bladder cooperate to cause cranial remodeling.

Other features and advantages of the present device will be come apparent from the following detailed description of the preferred embodiment made with reference to the accompanying drawings, which form a part of the specification.

BRIEF DESCRIPTION OF THE DRAWINGS

In the accompanying drawings, which are incorporated in and constitute a part of this specification, numerous embodiments of the device described are illustrated, and together with the general description above, and the description below, exemplify the device of the present application.

DESCRIPTION OF THE BEST MODES OF THE DEVICE OF THE PRESENT APPLICATION

Figure 1:
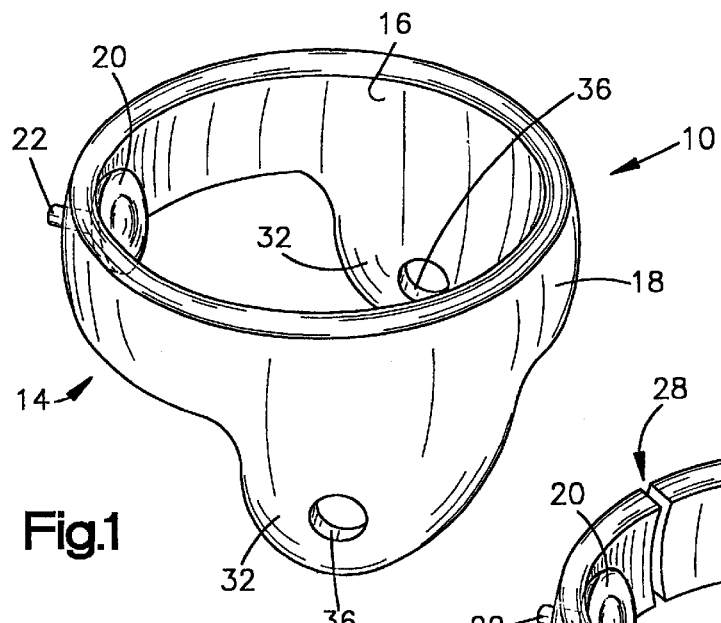
FIG. 1 is a perspective view of the cranial remodeling headpiece of the present invention.
Figure 3:
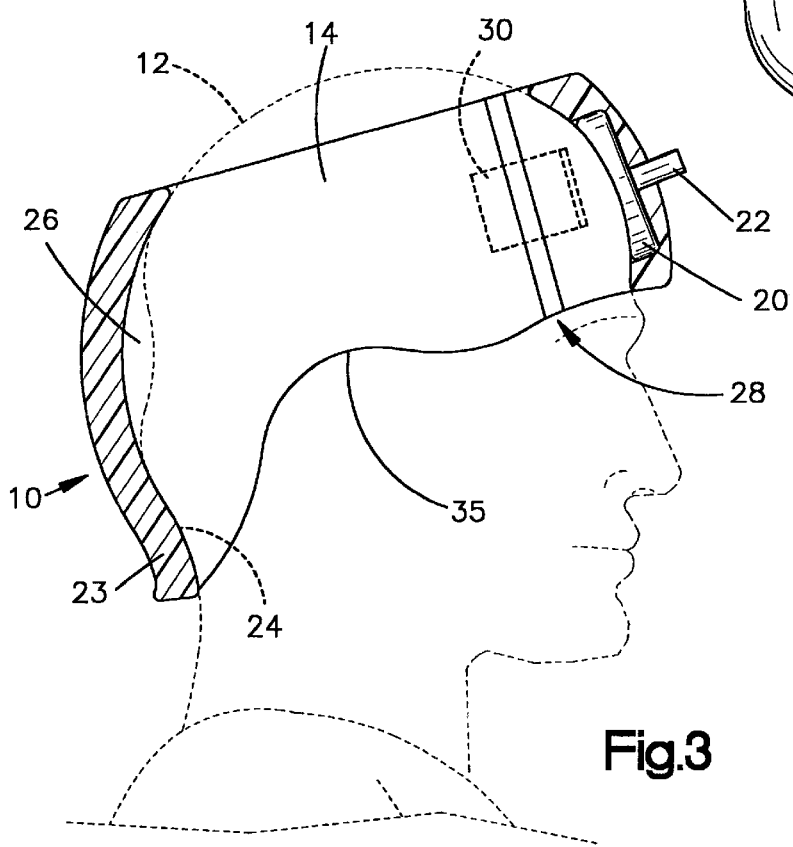
FIG. 3 is a side, cross-sectional view of an alternate embodiment of the cranial remodeling headpiece of the present invention, shown on a user's head.

The present invention is a cranial modeling orthosis 10 for use with an irregularly shaped skull 12. The orthosis induces directed cranial growth, cranial remodeling or postoperative cranial remodeling to achieve a desired skull shape. The orthosis 10 may be used for treatment of positional plagiocephaly and postoperative craniectomy/craniotomy for craniosynostosis. As illustrated in FIG. 1, the orthosis 10 preferably includes a headpiece 14 having an inner wall 16 and an outer wall 18, and one or more inflatable bladders 20 located on the inner wall 16. The headpiece 14 is preferably a clear polymer, and the bladders 20 are also preferably made of a clear polymer. This allows visual inspection of the skull 12 to ensure proper fit of the headpiece 14, to monitor cranial remodeling, and to watch for the development of induced iseschemia or pressure sores. Bladders 20 are preferably clear bladders with valves 22 extending through the headpiece 14 as illustrated. In a preferred embodiment, the bladders 20 are recessed within the inner wall 16 of the headpiece 14 so that they are flush with the inner wall 16, as shown in FIG. 3. The bladders 20 are commercially available from a variety of sources, and may be manufactured, by way of example, of CORDORA™ Nylon or other suitable conventional polymer materials.

Figure 4:
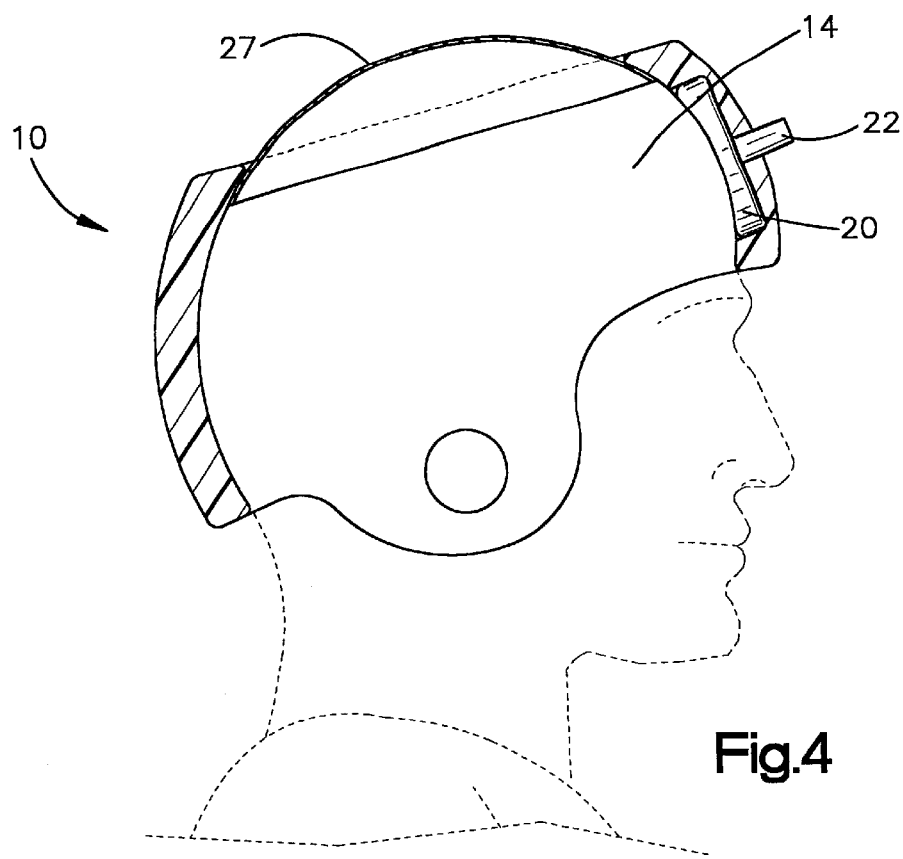
FIG. 4 is a cross-sectional view of another alternate embodiment of the cranial remodeling headpiece of the present invention, shown on a user's head.

The headpiece 14 is preferably rigid or non-deformable and is manufactured of a clear polymer, such as SURLYN™. In the embodiment shown in FIGS. 1–3, the headpiece 14 is a band shaped to fit around the perimeter of the skull 12. The headpiece may also include lower portion 23 (FIG. 3) which conforms to and preferably engages the nuchal ridge 24 and occiput of the user's skull. Additional padding (not shown) may be placed in the lower portion 23 to provide better engagement with the nuchal ridge 24 and occiput. The headpiece 14 is shaped to generally conform to the shape of the skull 12. However, as illustrated in FIG. 3, at least one recess 26 or area of compliance is formed in the headpiece 14 wherein the headpiece departs from the contour of the unmolded skull. The recess 26 provides a volume into which the skull 12 may be remodeled or grow to achieve the desired skull shape. Because the pressure applied by the bladders 20 is intended to remodel or direct growth the skull into the recess 26, the bladders 20 are spaced from the recess 26 at sufficient angles and distances to apply pressure and direct the skull toward the recess. Accordingly, when the orthosis 10 is placed on the user's head, and the bladders 20 are inflated to the appropriate level, the recess 26 and the expanded bladders cooperate to cause the desired cranial modeling or directed growth. It is believed that the remodeling can be partially attributed to reformation of the skull, and partially attributed to directed growth of the skull. If so desired, the orthosis 10 may also include a top cover 27 (FIG. 4) which extends above the headpiece 14 and covers the top of the user's skull. The top cover 27 may be manufactured of a variety of materials, including elastic, fabric, or other materials.

The headpiece may also include one or more areas of compliance in conjunction with, or in place of, the recess 26. The area of compliance is a compliant volume into which the skull may be remodeled or be growth directed. For example, the area of compliance may be padding or other compliant material which can be compressed by the remodeled or growing skull. Additionally, when the headpiece includes one or more discontinuities 28, the headpiece may be expanded by the growing/remodeled skull, thereby widening the discontinuity or discontinuities. In this case, the area of compliance is the entire headpiece 14.

Figure 2:
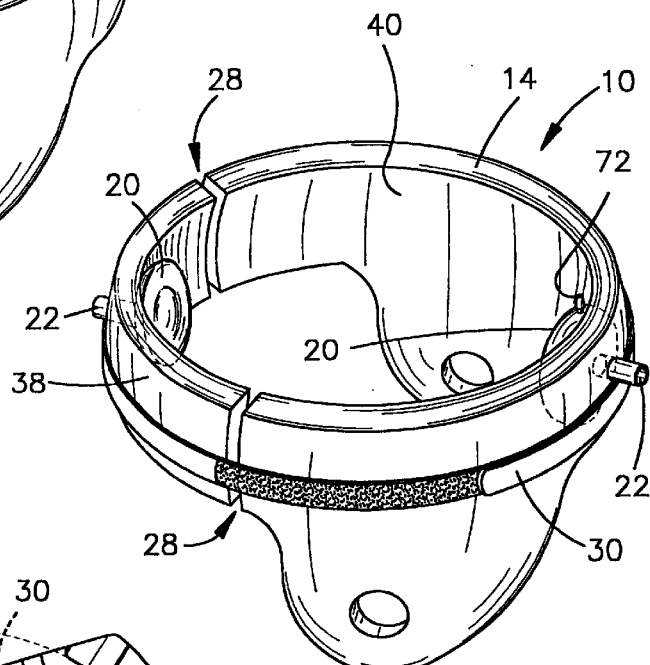
FIG. 2 is a perspective view of an alternate embodiment of the cranial remodeling headpiece of the present invention.
Figure 5:
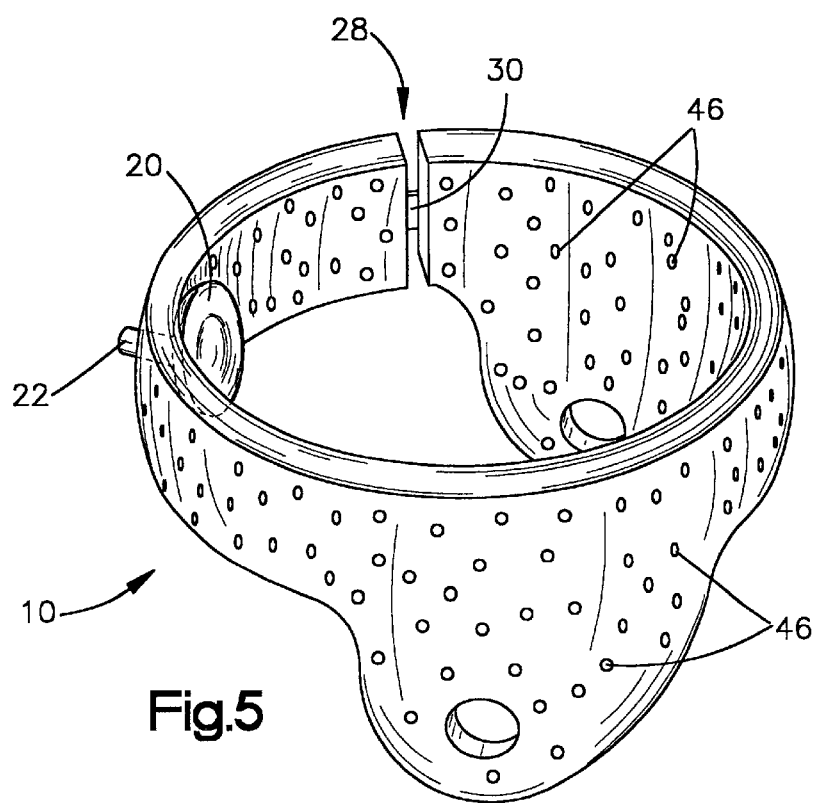
FIG. 5 is a perspective view of an yet another alternate embodiment of the cranial remodeling headpiece of the present invention.
Figure 6:
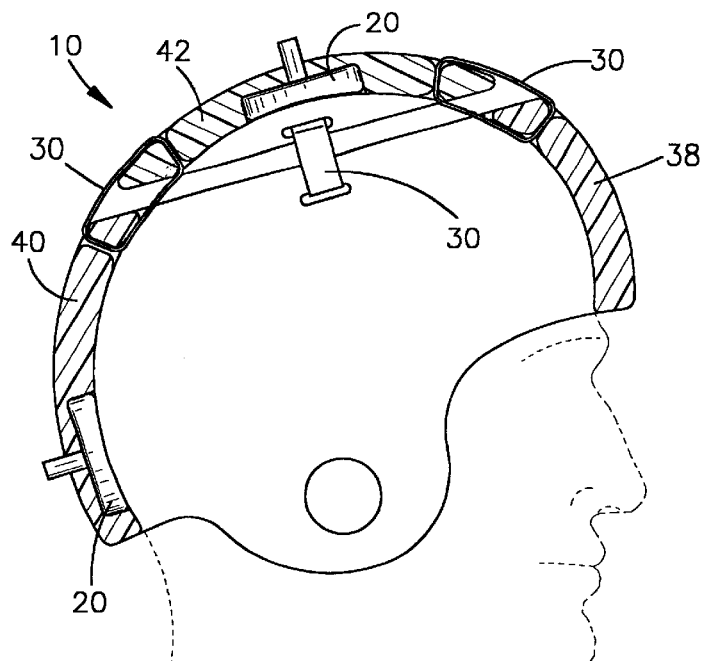
FIG. 6 is a side, cross-sectional view of an embodiment of the cranial remodeling headpiece of the present invention, shown on a user's head.
Figure 7:
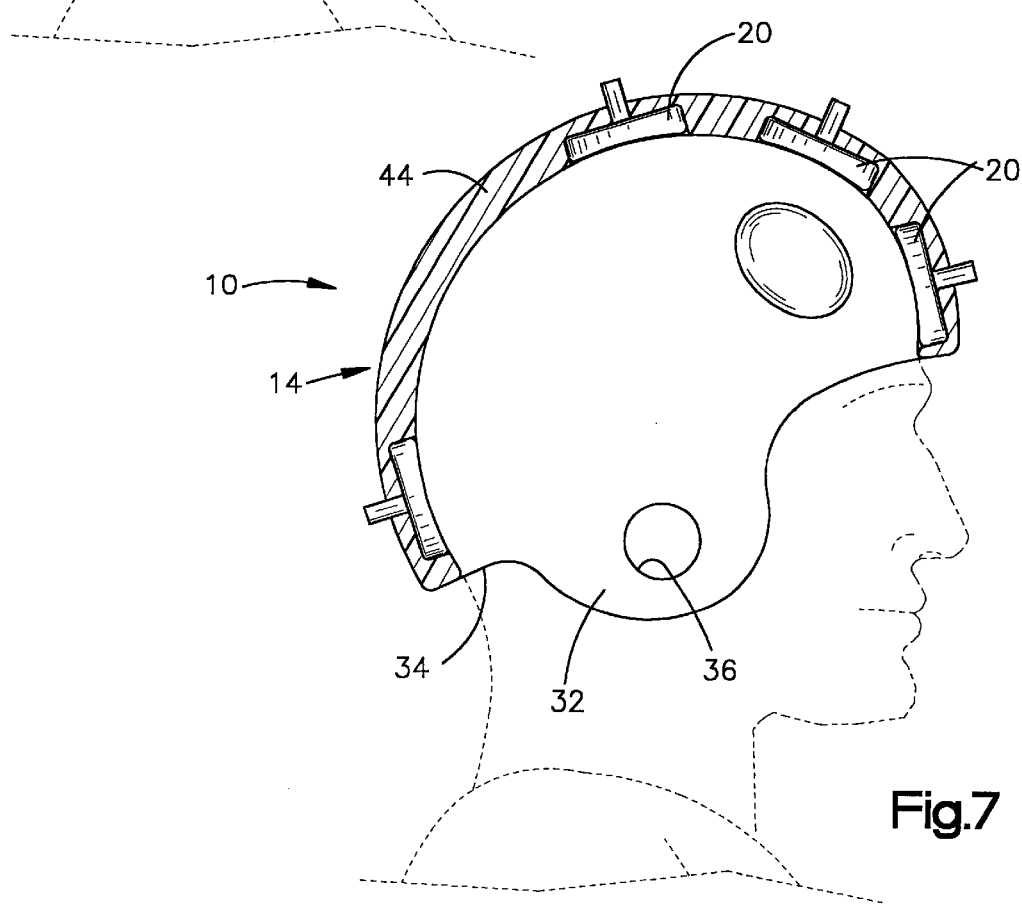
FIG. 7 is a cross-sectional view of another alternate embodiment of the cranial remodeling headpiece of the present invention, shown on a user's head.
Figure 11:
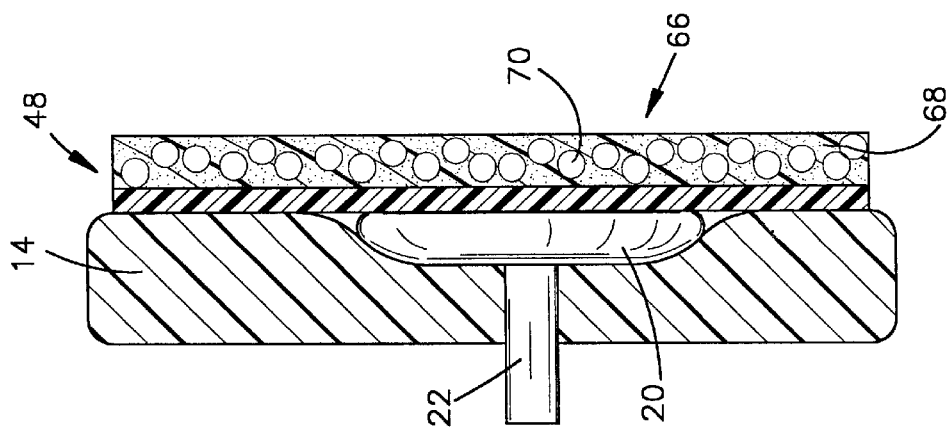
FIG. 11 is a detail cross-sectional view of a portion of the cranial remodeling headpiece of the present invention showing an intermediate layer and a pressure sensor layer.
Figure 10:
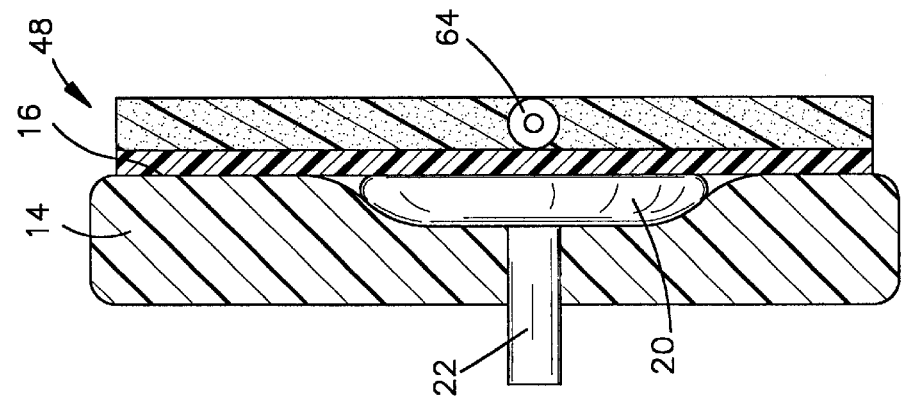
FIG. 10 is a detail cross-sectional view of a portion of the cranial remodeling headpiece of the present invention illustrating a sensor in the intermediate layer.

As shown in FIGS. 3 and 5, the headpiece may also include an axially extending discontinuity 28. The discontinuity 28 provides flexibility to the orthosis 10 to aid in donning and doffing the headpiece 14. Fastener 30 bridging the discontinuity 28 may be provided so that once the headpiece is properly positioned on the user's head, the fastener 30 may be closed to secure the headpiece 14. Fastener 30 may take a variety of forms well known in the art, including VELCRO® straps, elastic bands, or other similar fasteners or connectors. As shown in FIG. 2, the fastener 30 may also take the form of a VELCRO® strap around the outer perimeter of the headpiece 14. The fasteners 30 may be tightened or otherwise adjusted to accommodate growth of the skull or cranial modification during the remodeling process. As illustrated in FIG. 2, the headpiece 14 may also be made from two separate pieces, such as a front portion 38 and a rear portion 40 separated by a pair of discontinuities 28. In this case, the front portion 38 and rear portion 40 are joined by fasteners 30 as described above. In yet another embodiment, as shown in FIG. 6, the headpiece 14 may include a front portion 38, a rear portion 40, and a top portion 42, and the portions are joined by fasteners 30 in the manner previously discussed. Finally, as shown in FIG. 7, the headpiece 14 may comprise a one-piece helmet 44 shaped to cover nearly the entire skull.

The orthosis 10 may include nearly any number of combinations of recesses 26 and bladders 20. In a preferred arrangement, a first bladder is located along the rear bottom edge of the headpiece so as to engage the nuchal ridge and/or occiput, and a second bladder is located at the top center of the headpiece to engage the top of the skull. The headpiece may include a pair of tabs 32 extending downwardly from the bottom edge 34 of the headpiece 14, each tab 32 having an earhole 36 provided therethrough (FIG. 7). In place of the tabs 32 and earhole 36, the headpiece 14 may have an arched portion 35 so that the headpiece rests above the user's ear as shown in FIG. 3. Any shape cut out or form which fits over the ear may be acceptable in place of the arched portion 35. FIG. 5 illustrates the use of air holes 46 which may be formed in the headpiece to aid in ventilation and comfort for the user.

Figure 9:
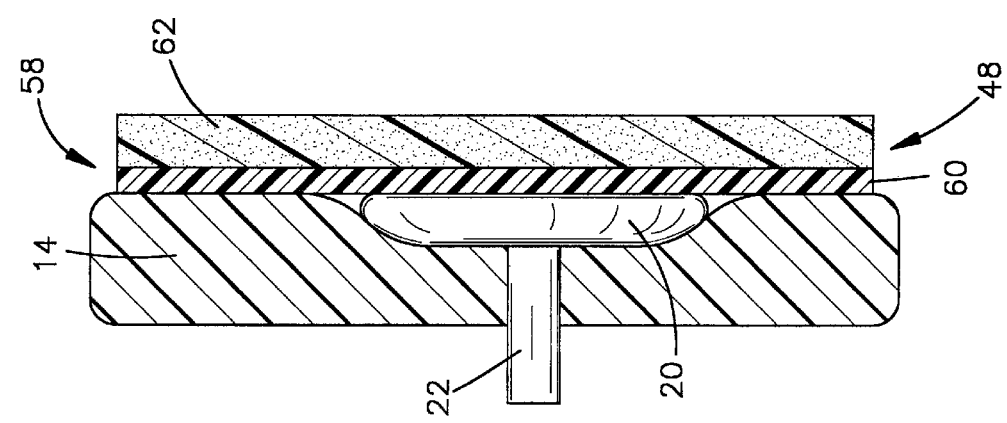
FIG. 9 is a detail cross-sectional view of a portion of the cranial remodeling headpiece of the present invention showing an alternate intermediate layer.
Figure 8:
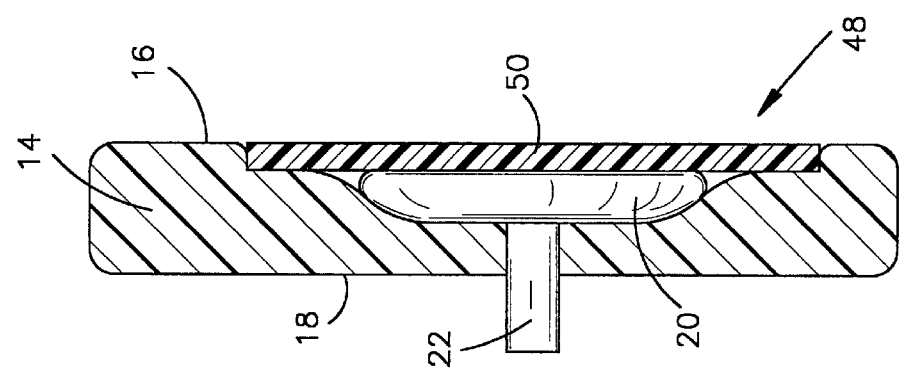
FIG. 8 is a detail cross-sectional view of a portion of the cranial remodeling headpiece of the present invention showing the intermediate layer.
Figure 12:
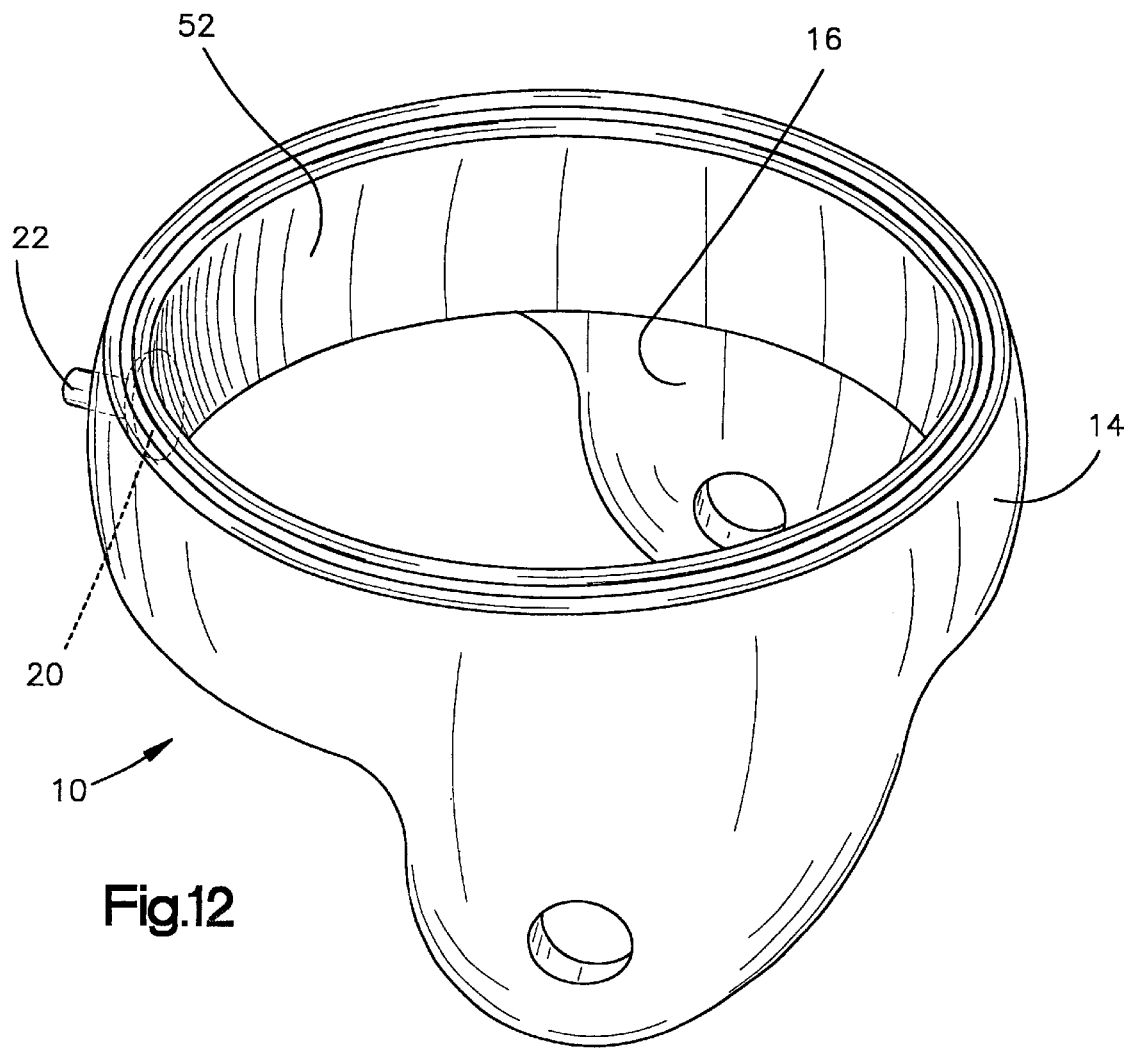
FIG. 12 is a perspective view of an alternate embodiment of the cranial remodeling headpiece of the present invention showing an intermediate layer.

As shown in FIGS. 8–11, the orthosis may further include an intermediate layer 48 located between the inner wall 16 and the user's head. The intermediate layer 48 assists in maintaining the position of the headpiece, provides padding, and aids in pressure control. The intermediate layer 48 may take the form of a plate 50 (FIG. 8) which aids in distributing the forces applied by the bladders 20 on the skull 12, and in this case the plate 50 is preferably rigid. The intermediate layer 48 may take the form of an elastomer layer 52 between the skull and the inner wall 16 (FIG. 12). The elastomer layer 52 may be an elongated strip which extends around a significant portion of the inner wall 16, or a ring which extends around the entire perimeter of the inner wall 16. In yet another embodiment, as shown in FIG. 9, the intermediate layer 48 is a composite 58 including a rigid plate 60 and an outer elastic layer 62. The composite acts 58 so as to reduce shear forces on the skull 12 and thereby increase the user's comfort. The composite 58 may also include another rigid plate as an outer layer (not shown) on top of the elastic layer 62. In all cases, the intermediate layer 48 is preferably sufficiently transparent so as to allow visual inspection of the skull.

The orthosis 10 may be modified to accommodate various sensors and the like for monitoring the condition of the user's scalp. For example, an oxygen sensor 64 (FIG. 10) may be adjacent the inner wall 16 and located to measure oxygen perfusion on the skull. A blood flow sensor (not shown) may be used in place of, or in conjunction with, the oxygen sensor 64. Furthermore, a pressure sensor may also be located adjacent the inner wall 16 in place of, or in conjunction with, the sensors described above. The pressure sensor may take the form of any pressure sensor well known in the art. However, in the preferred embodiment of FIG. 11 the pressure sensor 66 is a polymer sheet 68 encapsulating one or more pockets of air 70. Once the orthosis has been placed on the user's head, the pressure applied by the orthosis may be roughly determined by visual inspection of the air pockets 70 in the polymer sheet. The more the air pockets 70 are deformed, the greater the applied pressure.

The present device 10 provides the ability to more precisely monitor the pressure applied to the skull during treatment. The pressures may be easily varied by inflating or deflating the air bladders 20. The use of a clear polymer headpiece 14 enables visual inspection of the scalp for skin blanching, which provides an indicator that compromised blood flow is being provided to the skin. Adequate blood flow is required in order to avoid development of pressure sores or pressure necrosis.

The orthosis 10 may also be used as a post-operative therapeutic device. For example, in the case of craniosynostosis, surgery may be necessary to open sutures in the skull that have closed prematurely. The orthosis 10 may be used after surgery to achieve the desired cranial remodeling before the suture(s) subsequently fuses. The orthosis of the present invention can be particularly valuable in such a procedure due to the limited time frame in which cranial remodeling is possible after the surgery. It is expected that there will be other uses of the present invention, both in conjunction with surgery or as a treatment by itself, beyond those specifically described herein.

Once the orthosis 10 is mounted on the user's skull 12, and the fasteners 30, if any, are secured, the bladders 20 may be inflated to a predetermined pressure. Conventional inflation devices, such as hand held air pumps that may include pressure monitors, may be used. In this manner, the pressures in the bladders 20 may be precisely controlled to control the pressure applied to the user's skull. The desired pressure in the bladder may be within the range of 18 to 25 mm Hg of pressure, but may reach higher pressures such as 35 mm Hg, or higher depending upon the desired application. Valves 22 are provided on the bladders so that pressure may be released at any time to remove the headpiece. Additionally, a safety valve or "pop-off" valve 72 may also be provided as shown in FIG. 2 which serves as a release when a predetermined bladder pressure is exceeded.

In order to form the present device to achieve the desired remodeling, a plaster of paris mold is first made of the subject's head. Once the negative mold is available, a positive mold of the head is made, for example, through filling the negative impression with plaster of paris slurry. Once it is cured or hardened the negative mold is removed. Plaster is then added to the positive mold as desired, to build up the asymmetric locations of the head to achieve the desired head shape. These "built-up" locations will correspond to recesses in the final headpiece. Plaster may also be added to accommodate the space required for bladders in their desired locations. Alternately, space templates may be placed on the positive head mold to accommodate the volume required for the bladders and recess or areas of compliance.

Once the desired head shape is obtained on the positive mold, a model or check headpiece is preferably formed. The check headpiece is manufactured of a cheaper material than the final headpiece and is formed to ensure proper fit before proceeding to the final headpiece. To manufacture the check headpiece, polymer material such as VIVAC™ is heated and conformed to the shape of the positive head mold. The mold and heated polymer material are then placed under a vacuum to conform the polymer as close to the shape of the head mold as possible. Once the polymer cools, the user may then be fitted with the check headpiece. If additional changes are required based on the fitting, the positive head mold may be reconfigured to achieve the desired shape.

Once the final desired shape of the head is obtained, the final headpiece material is heated and bubble or drape vacuum formed to the mold as described above. Once the final headpiece is cooled, additional finishing to smooth and polish the material may be applied.

Due to growth and/or remodeling of the user's skull, it may become necessary to change the shape or fit of the headpiece beyond that permitted by the fasteners. To modify the headpiece, the positive head mold is further reconfigured to accommodate the growth or remodeling changes. The headpiece may then either be recast, or the same headpiece may preferably be reheated and conformed to the reconfigured positive head mold.

Some of the factors which influence the success of remodeling devices includes the patient's age, the anatomic regions, calvarial mineralization, as well as the intervals of time the device is used and the amount of force applied. An example of the average length of time the present device would be used is approximately 4–5 months, but the device may be used for as short or long as necessary. The device is preferably monitored by a medical care giver every two weeks to once per month. Various measurements such as cranial asymmetry, cranial base asymmetry, external auditory canal position, and cranial growth may be taken to monitor craniofacial growth.

The preferred form of the cranial remodeling orthosis has been described above. However, with the present disclosure in mind it is believed that obvious alterations to the preferred embodiments, to achieve comparable features and advantages in other assemblies, will become apparent to those of ordinary skill in the art.

We claim:

1. A cranial remodeling orthosis for inducing directed growth and remodeling of an irregularly-shaped skull, said orthosis comprising:

a headpiece having an outer wall and an inner wall, said inner wall being shaped to receive the skull and having a recess formed therein to provide a volume in which the skull may be remodeled;

a first expandable bladder located on said inner wall of said headpiece;

whereby when said orthosis is placed on the skull and said bladder is expanded, said recess and said expanded bladder cooperate to cause cranial remodeling and directed growth; and an intermediate layer between said bladder and the skull, said intermediate layer comprising a generally rigid plate.

2. The orthosis of claim 1 wherein said plate is sufficiently transparent so as to allow visual inspection of the skull therethrough.

3. The orthosis of claim 2 wherein said intermediate layer is an elastomeric polymer.

4. A cranial remodeling orthosis for inducing directed growth and remodeling of an irregularly-shaped skull, said orthosis comprising:

a headpiece having an outer wall and an inner wall, said inner wall being shaped to receive the skull and having a recess formed therein to provide a volume into which the skull may be remodeled;

a first expandable bladder located on said inner wall of said headpiece;

whereby when said orthosis is placed on the skull and said bladder is expanded, said recess and said expanded bladder cooperate to cause cranial remodeling and directed growth; and an intermediate layer between said bladder and the skull, said intermediate layer comprising a composite plate including two outer layers and a middle elastic layer, whereby said composite plate reduces shear forces on the skull.

5. A cranial remodeling orthosis for inducing directed growth and remodeling of an irregularly-shaped skull, said orthosis comprising:

a headpiece having an outer wall and an inner wall, said inner wall being shaped to receive the skull and having a recess formed therein to provide a volume into which the skull may be remodeled;

a first expandable bladder located on said inner wall of said headpiece;

whereby when said orthosis is placed on the skull and said bladder is expanded, said recess and said expanded bladder cooperate to cause cranial remodeling and directed growth; and an oxygen sensor adjacent said inner wall for measuring oxygen perfusion on the scalp.

6. A cranial remodeling orthosis for inducing directed growth and remodeling of an irregularly-shaped skull, said orthosis comprising:

a headpiece having an outer wall and an inner wall, said inner wall being shaped to receive the skull and having a recess formed therein to provide a volume into which the skull may be remodeled; and a first expandable bladder located on said inner wall of said headpiece;

whereby when said orthosis is placed on the skull and said bladder is expanded, said recess and said expanded bladder cooperate to cause cranial remodeling and directed growth; and a blood flow sensor adjacent said inner wall for measuring blood flow on the scalp.

7. A cranial remodeling orthosis for inducing directed growth and remodeling of an irregularly-shaped skull, said orthosis comprising:

a headpiece having an outer wall and an inner wall, said inner wall being shaped to receive the skull and having a recess formed therein to provide a volume into which the skull may be remodeled;

a first expandable bladder located on said inner wall of said headpiece;

whereby when said orthosis is placed on the skull and said bladder is expanded, said recess and said expanded bladder cooperate to cause cranial remodeling and directed growth; and a pressure sensor adjacent said inner wall for measuring pressure applied by said orthosis on the scalp.

8. The orthosis of claim 7 wherein said pressure sensor is a polymer encapsulating a pocket of air, whereby the applied pressure may be evaluated by visual inspection of said pressure sensor.

9. A cranial remodeling orthosis for inducing directed growth and remodeling of an irregularly-shaped skull, said orthosis comprising:

a rigid headpiece having an outer wall and an inner wall, said inner wall having a shape that is complimentary to the irregularly-shaped skull except for a recess formed therein, said recess having a shape that is not complimentary to the irregularly-shaped skull and defining a volume into which the skull may be remodeled, said headpiece comprising front and rear portions and being open across a top portion of the skull; and an expandable bladder located on said inner wall of said headpiece;

whereby when said orthosis is placed on the skull and said bladder is expanded, said headpiece and said expanded bladder cooperate to cause cranial remodeling and directed growth of the skull into said volume defined by said recess in said inner wall.

10. The orthosis of claim 7 wherein said headpiece and said bladder are sufficiently transparent to allow visual inspection of the skull therethrough.

11. The orthosis of claim 9 further comprising an intermediate layer between said bladder and the skull.

12. The orthosis of claim 9 wherein said headpiece includes an axially extending discontinuity formed therein to provide flexibility to said orthosis.

13. The orthosis of claim 12 further comprising a fastener bridging said discontinuity for securing said orthosis around the skull.

14. The orthosis of claim 9 wherein said front and rear portions are joined by a pair of fasteners.

15. The orthosis of claim 9 wherein said bladder includes a safety valve to allow depressurization of said bladder to limit the maximum pressure applied to the skull.

16. The orthosis of claim 9 wherein said headpiece has at least one hole formed therein to provide air circulation to the skull.

17. The orthosis of claim 9 wherein said headpiece is a band shaped to fit around the perimeter of the skull.

18. A cranial remodeling orthosis for inducing directed growth and remodeling of an irregularly-shaped skull, said orthosis comprising:

a headpiece having an outer wall and an inner wall, said headpiece having a shape that is complimentary to the irregularly-shaped skull except for a recess formed in said inner wall, said recess having a shape that is not complimentary to the irregularly-shaped skull and defining a volume into which the skull may be remodeled; and an inflatable bladder positioned in said headpiece, said bladder, when uninflated, being recessed in said inner wall of said headpiece;

whereby when said orthosis is placed on the skull and said bladder is inflated, said headpiece and said inflated bladder cooperate to cause cranial remodeling and directed growth of the skull into said volume defined by said recess in said inner wall.

19. The orthosis of claim 18 wherein said headpiece is made of a rigid material.

20. The orthosis of claim 18 wherein said headpiece and said bladder are sufficiently transparent to allow visual inspection of the skull therethrough.

21. The orthosis of claim 18 further comprising an intermediate layer between said bladder and the skull.

22. The orthosis of claim 18 wherein said headpiece includes an axially extending discontinuity formed therein to provide flexibility to said orthosis.

23. The orthosis of claim 22 further comprising a fastener bridging said discontinuity for securing said orthosis around the skull.

24. The orthosis of claim 18 wherein said headpiece comprises a front portion and a rear portion, said front and rear portion being joined by a pair of fasteners.

25. The orthosis of claim 18 wherein said headpiece comprises a front portion, a rear portion, and a top portion for fitting on top of the skull, said portions being joined by fasteners.

26. The orthosis of claim 18 further comprising a plurality of inflatable bladders.

27. The orthosis of claim 26 wherein said plurality of bladders are spaced from said recess at sufficient angles and distances so that pressure applied by said bladders directs the skull to remodel or grow into said volume defined by said recess.

28. The orthosis of claim 18 wherein said bladder includes a safety valve to allow depressurization of said bladder to limit the maximum pressure applied to the skull.

29. The orthosis of claim 18 wherein said headpiece has at least one hole formed therein to provide air circulation to the skull.

30. The orthosis of claim 18 wherein said headpiece is a band shaped to fit around the perimeter of the skull.

31. The orthosis of claim 30 wherein said headpiece is a helmet shaped to partially cover the skull.

\* \* \* \* \*

UNITED STATES PATENT AND TRADEMARK OFFICE
CERTIFICATE OF CORRECTION

PATENT NO.   : 6,422,957 B1
DATED        : July 23, 2002
INVENTOR(S)  : David C. Winter and S. Curtis Nye It is certified that error appears in the above-identified patent and that said Letters Patent is hereby corrected as shown below:

Column 7,
Line 21, change "1.18" to -- 118 --

Column 9,
Line 60, change "engag" to -- engage --

Column 13,
Line 12, delete "the"

Column 14,
Line 10, change "goal-assembly" to -- goal assembly --
Line 13, change "An adjustable method for" to -- The method for adjusting the height of --

Signed and Sealed this

Fourth Day of February, 2003

JAMES E. ROGAN
*Director of the United States Patent and Trademark Office*